US012653788B2

(12) United States Patent
Kulczar et al.

(10) Patent No.: US 12,653,788 B2
(45) Date of Patent: Jun. 16, 2026

(54) PHARMACEUTICAL COMPOSITION OF A PYRAZOLE COMPOUND DISPERSED IN A POLYMER MATRIX

(71) Applicant: Intervet Inc., Madison, NJ (US)

(72) Inventors: Christopher D. Kulczar, Jersey City, NJ (US); Luke Ryan Schenck, Yardley, PA (US); Yongjun Li, New York, NY (US); Alfred C.F. Rumondor, Raritan, NJ (US)

(73) Assignee: Intervet Inc., Rahway, NJ (US)

( * ) Notice: Subject to any disclaimer, the term of this patent is extended or adjusted under 35 U.S.C. 154(b) by 959 days.

(21) Appl. No.: 17/785,665

(22) PCT Filed: Dec. 18, 2020

(86) PCT No.: PCT/EP2020/086918
§ 371 (c)(1),
(2) Date: Jun. 15, 2022

(87) PCT Pub. No.: WO2021/123088
PCT Pub. Date: Jun. 24, 2021

(65) Prior Publication Data

US 2023/0062746 A1 Mar. 2, 2023

Related U.S. Application Data

(60) Provisional application No. 62/951,162, filed on Dec. 20, 2019.

(51) Int. Cl.
*A61K 9/20* (2006.01)
*A61K 31/4439* (2006.01)
*A61P 17/00* (2006.01)

(52) U.S. Cl.
CPC .......... *A61K 9/2054* (2013.01); *A61K 9/2013* (2013.01); *A61K 9/2095* (2013.01); *A61K 31/4439* (2013.01); *A61P 17/00* (2018.01)

(58) Field of Classification Search
CPC .............. A61K 31/4439; A61K 9/2054; A61K 9/2013; A61K 9/2095
See application file for complete search history.

(56) References Cited

U.S. PATENT DOCUMENTS

| | | | |
|---|---|---|---|
| 8,263,128 B2 | 9/2012 | Curatolo | |
| 10,875,847 B2 * | 12/2020 | Fuller | A61P 27/02 |

FOREIGN PATENT DOCUMENTS

| | | | | |
|---|---|---|---|---|
| CN | 101668527 A | 3/2010 | | |
| CN | 102231990 A | 11/2011 | | |
| CN | 104936589 A | 9/2015 | | |
| CN | 110062754 A | 7/2019 | | |
| WO | 2008103914 A1 | 8/2008 | | |
| WO | 2010019239 A2 | 2/2010 | | |
| WO | 2013041042 A1 | 3/2013 | | |
| WO | 2013130669 A1 | 9/2013 | | |
| WO | 2014114575 A1 | 7/2014 | | |
| WO | WO-2018108969 A1 * | 6/2018 | | A61P 17/00 |
| WO | 2019091438 A1 | 5/2019 | | |

OTHER PUBLICATIONS

Harskamp et al., Immunology of Atopic Dermatitis: Novel Insights into Mechanisms and Immunomodulatory Therapies, Seminars in Cutaneous Medicine and Surgery, 2013, 132-139, 32.
Hill, P.B., Development of an owner-assessed scale to measure the severity of pruritus in dogs, Veterinary Dermatology, 2007, 301-308, 18.
Huang, Y. et al., Fundamental aspects of solid dispersion technology for poorly soluble drugs, Acta Pharmaceutica Sinica B, 2014, 18-25, 4(1).
Nuttall et al., Canine Atopic Dermatitis—what have we learned?, Veterinary Record, 2013, 201-207, 172(8).
Olivry, Thierry, Validation of the Canine Atopic Dermatitis Extent and Severity Index (CADESI)-4, a simplified severity scale for assessing skin lesions of atopic dermatitis in dogs, Veterinary Dermatology, 2014, 77-e25, 25.
Rahman et al., The Pathology and Immunology of Atopic Dermatitis, Inflammation & Allergy—Drug Targets, 2011, 486-496, 10.
Vasconcelos, T. et al., Solid dispersions a strategy to improve oral bioavailability of poor water soluble drug, Drug Discovery Today, 2007, 1068-1075, 12.

* cited by examiner

*Primary Examiner* — Kevin E Weddington
(74) *Attorney, Agent, or Firm* — David J. Kerwick

(57) ABSTRACT

A pharmaceutical composition of pyrazole compound dispersed in a polymer matrix and a method of using the same to treat atopic dermatitis.

11 Claims, 3 Drawing Sheets

PHARMACEUTICAL COMPOSITION OF A PYRAZOLE COMPOUND DISPERSED IN A POLYMER MATRIX

CROSS-REFERENCE TO RELATED APPLICATIONS

This application is a national stage entry under 35 U.S.C. § 371 of PCT/EP2020/086918 filed Dec. 18, 2020, which claims priority to U.S. application 62/951,162 filed Dec. 20, 2019, the contents of which are hereby incorporated by reference in their entireties.

BACKGROUND

WO 2018/108969 discloses compounds of formula I which are selective Janus kinase (JAK) inhibitors, and as such are useful for the treatment of JAK-mediated diseases such as atopic dermatitis, arthritis, and cancer. Specifically, 1-[(3R,4S)-4-cyanotetrahydropyran-3-yl]-3-[(2-fluoro-6-methoxy-4-pyridyl)amino]pyrazole-4-carboxamide (I) is disclosed.

Formula (I)

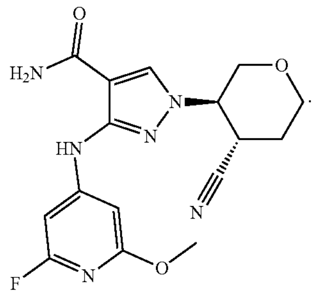

In a cIL-31 induced pruritus study, the compound of Formula (I) significantly suppressed pruritus with respect to placebo and in a similar magnitude to oclacitinib (Apoquel®). Apoquel® is a commercially available product for the treatment of atopic dermatitis in dogs. Also disclosed are methods of treating atopic dermatitis by oral administration of compound (I).

WO 2013/041042 discloses pyrazole carboxamides as Janus kinase inhibitors that are useful for the treatment of rheumatoid arthritis, asthma, chronic obstructive pulmonary disease (COPD) and cancer. The compounds of this disclosure are of the following formula.

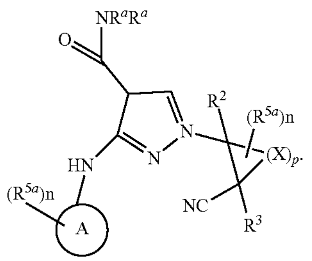

Atopic dermatitis (AD) is a relapsing pruritic and chronic inflammatory skin disease, that is characterized by immune system dysregulation and epidermal barrier abnormalities in humans. The pathological and immunological attributes of atopic dermatitis have been the subject of extensive investigations [reviewed in Rahman et al. *Inflammation & Allergy-drug target* 10:486-496 (2011) and Harskamp et al., *Seminar in Cutaneous Medicine and Surgery* 32:132-139 (2013)]. Atopic dermatitis is also a common condition in companion animals, especially dogs, where its prevalence has been estimated to be approximately 10-15% of the canine population. The pathogenesis of atopic dermatitis in dogs and cats [reviewed in Nuttall et al., *Veterinary Records* 172(8):201-207 (2013)] shows significant similarities to that of atopic dermatitis in man including skin infiltration by a variety of immune cells and $CD4^+$ Th2 polarized cytokine milieu including the preponderance of IL-4, IL-13, and IL-31. In addition, IL-22 has been implicated in the exaggerated epithelial proliferation leading to epidermal hyperplasia that is characteristic of atopic dermatitis.

Applicants have found that dispersion of the compound of Formula (I) in a hydroxypropyl methylcellulose acetate succinate (HPMCAS) polymer matrix resulted in improved bioavailability of the compound of Formula (I).

SUMMARY OF THE INVENTION

An embodiment of the invention is a pharmaceutical composition comprising a pharmaceutically effective amount of 1-[(3R,4S)-4-cyanotetrahydropyran-3-yl]-3-[(2-fluoro-6-methoxy-4-pyridyl)amino]pyrazole-4-carboxamide dispersed in a HPMCAS polymer matrix; and a pharmaceutically acceptable carrier.

Another embodiment of the invention is a method of treating atopic dermatitis comprising orally administering to an animal in need of an effective amount of the above pharmaceutical composition.

Another embodiment is a process of making the pharmaceutical composition.

DETAILED DESCRIPTION

Figure 1:
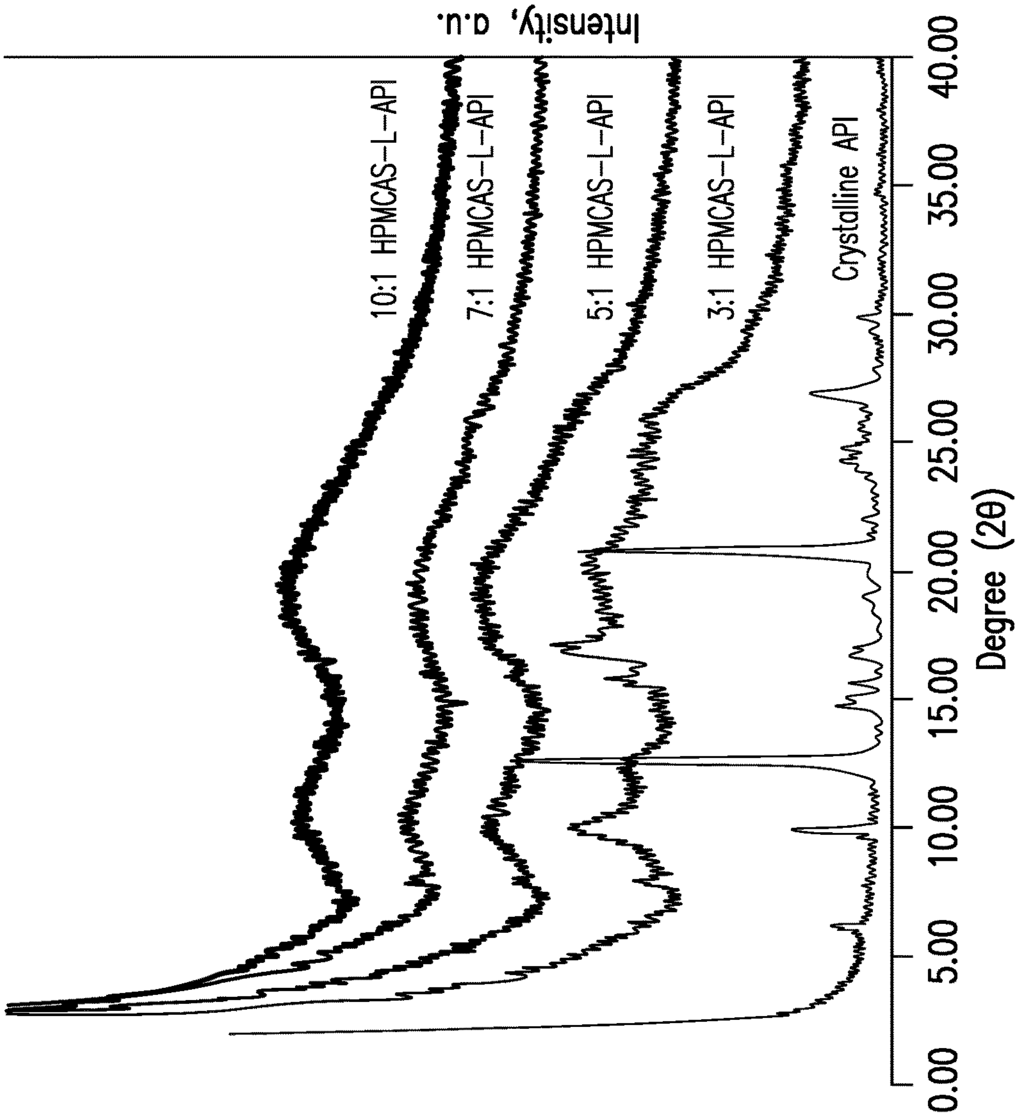
FIG. 1—Powder X-ray diffraction (PXRD) to determine the amount of amorphous compound present in the amorphous solid dispersion (ASD).

Applicants have developed a formulation of 1-[(3R,4S)-4-cyanotetrahydropyran-3-yl]-3-[(2-fluoro-6-methoxy-4-pyridyl)amino]pyrazole-4-carboxamide, the compound of Formula (I)

(I)

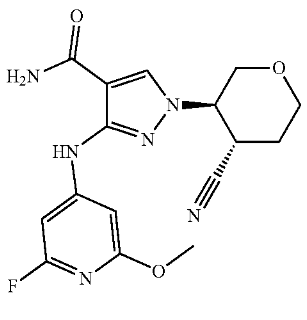

The compound of Formula (I) is a selective Janus kinase (JAK) inhibitor which However, the compound of Formula (I) is a poorly water soluble compound. Generally, poor water solubility of a pharmaceutically active agent results in poor oral bioavailability in dogs, and hence, in poor biological efficacy of the agent. However, the compound of Formula (I) is a poorly water soluble compound. The poor water solubility results in poor oral bioavailability in dogs, often below 50%. The log P of the compound of Formula (I) is calculated to be 1.25 (Chem Draw and Insight for Excel). To increase solubilization and promote bioavailability, Applicants have dosed the compound in the amorphous state as part of an amorphous solid dispersion (ASD). Due to the compound's high melting point (>250° C.) and low solubility in volatile solvents such as isopropanol, acetone, and dichloromethane, conventional techniques of producing ASDs such as spray drying and hot melt extrusion were not conducive for manufacture of an ASD containing the compound of Formula (I). Therefore, the ASD was manufactured by co-precipitation or cPAD (co-precipitated amorphous dispersion). In this process, the compound and a polymer were dissolved into a solvent. The compound-polymer solution was then rapidly precipitated in an anti-solvent under high shear in a rotor-stator homogenizer. and the compound-polymer amorphous solid dispersion was formed.

Applicants have now found that the using the compound of Formula (I) in an amorphous state as part of an amorphous solid dispersion resulted in a formulation with improved bioavailability when compared to a formulation with the compound of Formula (I) in a crystalline form.

Substantially in an amorphous form means at least 80% of the compound is in amorphous form, preferably at least 90% or 95% of the compound is in amorphous form. Percent amorphous form versus crystalline form is measured by PXRD or NMR.

A tablet is a solid dosage form containing an active ingredient with or without suitable excipients and prepared by either compression or molding. A compressed tablet is a tablet formed by compression.

A solid dispersion is dispersion of a drug in a solid matrix wherein the matrix is a small molecule or a polymer. Methods of preparing solid dispersions are melt extrusion, spray drying and co-precipitation. See Huang et al., Acta Pharmaceutica Sinica B 2014; 4(1), pp 18-25. When the active ingredient is in an amorphous form, this is called an amorphous solid dispersion (ASD).

In a drug polymer matrix, several polymer chains physically entrap the drug molecules. In the idea situation, the drug molecules are evenly distributed throughout the polymer matrix.

Hydroxypropyl methylcellulose acetate succinate (HPMCAS) polymers also known as hypromellose acetate succinate are commonly used in oral pharmaceutical formulations as a film coating, as well as an enteric coating material for tablets or granules. These polymers are solubility enhancing agents for solid dispersion formulations. HPMCAS polymers have been used as carriers for amorphous solid dispersion of poorly water-soluble drugs that are prepared by spray drying and hot melt extrusion. Hydroxypropyl methylcellulose acetate succinate polymers are a mixture of succinic acid and acetic acid ethers of hydroxypropyl methylcellulose. HPMCAS polymers are available in several grades which vary in the acetyl, succinoyl, methoxyl and hydroxylpropyl contents. For example, the AquaSolve™ brand of hydroxypropyl methylcellulose acetate succinate (Ashland) has three grades as indicated below.

| HPMCAS Grade | Acetyl content | Succinoyl content | Methoxyl content | Hydroxylpropyl content |
|---|---|---|---|---|
| L | 5-9% | 14-18% | 20-24% | 5-9% |
| M | 7-11% | 10-14% | 21-25% | 5-9% |
| H | 10-14% | 4-8% | 22-26% | 6-10% |

In an embodiment, the HPMCAS polymer is grade L. In an embodiment, the HPMCAS polymer is grade M. In an embodiment, the HPMCAS polymer is grade H. In an embodiment, the HPMCAS polymer is a mixture of two or more grades.

In an embodiment, the pharmaceutical carrier comprises one or more excipients selected from a filler, a lubricant, a binder, an anti-nucleating agent and a disintegrant.

The pharmaceutical composition may contain one or more lubricants. Lubricants reduce the friction between the formed tablet and the wall of the die used to form the tablet, thus making it easier for the tablet to be removed from the die. Examples of lubricants are magnesium stearate, talc, colloidal silica, and sodium stearyl fumarate. In an embodiment, the lubricant is magnesium stearate.

The pharmaceutical composition may contain one or more glidants. Glidants are used to improve flowability. In an embodiment, the glidant is colloidal silica, talc or mixtures thereof.

The pharmaceutical composition further comprises one or more fillers/compression aids. Fillers/compression aids are used to increase the bulk or volume of a pharmaceutical dosage form that has a low dose active ingredient and to increase the mechanical strength of a dosage form such as a tablet. Examples of fillers are microcrystalline cellulose (MCC) (Avicel PH102), lactose anhydrous, lactose monohydrate (Fast Flo 316), starch, polyols (e.g. sorbitol, mannitol, maltitol), maltodextrin, dextrose, calcium phosphate, and calcium sulphate. In an embodiment, the filler is microcrystalline, lactose monohydrate cellulose or mixtures thereof.

The pharmaceutical composition further comprises one or more disintegrants. Disintegrants help to make a tablet break into smaller pieces once in contact with a liquid. Examples of disintegrants are sodium starch glycolate (Type A), croscarmellose sodium, and crospovidone. In an embodiment, the disintegrant is sodium starch glycolate (Type A).

The pharmaceutical composition further comprises one or more binders. Binders are used to increase the mechanical strength of a dosage form such as a tablet. Binders are also used to aid granule formation in the (wet or dry) granulation process. Formation of granules increase (drug) content uniformity and flowability of the final blend. Examples of binders are PVP, hydroxypropyl methylcellulose (HPMC) and hydroxypropyl celluose (HPC). In an embodiment, the binder is hydroxypropyl celluose (HPC).

The pharmaceutical composition further comprises one or more anti-nucleating agents. An anti-nucleating agent inhibits crystallization of a formulation. Examples include cellulose based polymers such as methylcellulose and hydroxypropylmethyl cellulose, poloxomers such as P68, P88, P98, P108, P125, P188, P237, P338, and P407, polyethylene glycols, polyvinyl alcohol (PVA), vinylpyrrolidone-vinyl acetate copolymers (VA64), polyvinylpyrrolidone (PVP), poly(lactic-co-glycolic acid) (PLGA), methyl cellulose A4C, hydroxypropyl methylcellulose E50 and polycaprolactone (PCL). In an embodiment, the anti-nucleating agent is methyl cellulose A4C or hydroxypropyl methylcellulose E50.

In an embodiment of the invention, the formulation is of the following composition:

| Ingredient | % (w/w) | Purpose |
|---|---|---|
| Active ingredient | 2 | Active |
| HPMCAS-L | 20 | polymer |
| Microcrystalline Cellulose | 45 | Filler |
| Lactose Monohydrate | 27 | Filler |
| Sodium Starch Glycolate (Type A) | 5 | Disintegrant |
| Magnesium Stearate | 1 | Lubricant |

In alternative embodiments of the invention, the concentration of the components of the formulation may vary as indicated below:

| Ingredient | % (w/w) | Purpose |
|---|---|---|
| Active ingredient | 0.5-10 | Active |
| HPMCAS-L | 10-30 | polymer |
| Microcrystalline Cellulose | 0-75* | Filler |
| Lactose Monohydrate | 0-75* | Filler |
| Sodium Starch Glycolate (Type A) | 0-10 | Disintegrant |
| Hydroxypropylcellulose | 0-5 | Binder |
| Magnesium Stearate | 0.25-1.5 | Lubricant |

*The combined w/w percentages of microcrystalline cellulose and lactose monohydrate must be at least 40%.

In embodiment, the pharmaceutical composition is a solid, preferably a tablet.

An embodiment of the invention is a solid pharmaceutical composition comprising a) a pharmaceutically effective amount of a compound of Formula (I)

Formula (I)

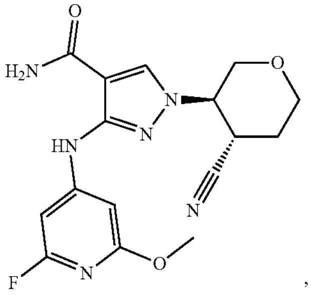

, dispersed in a hydroxypropyl methylcellulose acetate succinate (HPMCAS) polymer matrix; and b) a pharmaceutically acceptable carrier;

wherein the compound of Formula (I) is present in substantially an amorphous form; and wherein the pharmaceutical composition is a tablet.

In an embodiment, the ratio of the polymer to the compound of Formula (I) in the dispersion is between about 1:1 to about 20:1 or between about 10:1 and about 5:1.

In an embodiment, the amount of the compound of Formula (I) in the pharmaceutical composition is between about 0.5 and about 10% or is between about 1.0 and about 5.0% or is about 2% (w/w).

In an embodiment, the amount of HPMCAS-L polymer in the pharmaceutical composition is between about 10 and about 30% or is between about 15 and about 25% or is about 20% (w/w).

Processes to Make the Amorphous Solid Dispersion (ASD) Formulations

In this process, an active ingredient (API) and a polymer ( ) were dissolved into a solvent. The API-Polymer solution was then rapidly precipitated in an anti-solvent. The precipitation was washed and dried. An amorphous solid dispersion of the API and the polymer was formed and compressed into tablets.

In an embodiment, the API is the compound of Formula (I).

In an embodiment, the polymer is hydroxypropyl methylcellulose acetate succinate, grade L In an embodiment, the solvent is dimethylacetamide (DMAc or DMA). DMAc is an organic compound with the formula $CH_3C(O)N(CH_3)_2$.

In an embodiment, the anti-solvent is an aqueous acidic solution with a pH of less than 5, preferably a hydrochloric acid, preferably 0.1 N HCl.

In an embodiment, the api-polymer precipitation from the solvent; anti-solvent was conducted under high shear in a rotor-stator homogenizer.

In an embodiment, the precipitation and wash conditions were a 1:10 solvent:ant-solvent precipitation followed by a 10× slurry wash followed by a 5× displacement wash.

In an embodiment, in the amorphous solid dispersion, the compound of Formula (I) and the HPMCAS-L polymer are in 10:1 ratio.

In an embodiment, in the amorphous solid dispersion, the compound of Formula (I) and the HPMCAS-L polymer are in 5:1 ratio.

In an embodiment, the surfactant, disintegrant, and anti-nucleating agent are added intra- or inter- the ASD. In an embodiment, the fillers, binders, lubricants are blended in after the ASD is formed and dried.

An embodiment of the invention is a process to make the above pharmaceutical compositions comprising i) dissolving the compound of Formula (I) and a polymer in a solvent;

ii) combing the solution of step i) with an anti-solvent to precipitate an amorphous solid dispersion of the compound of Formula (I) in the polymer;

iii) blending the amorphous solid dispersion of step ii) with a pharmaceutically acceptable carrier and iv) compressing the product of step iii) into a tablet to produce the pharmaceutical composition;

wherein the solvent is dimethyl acetamide (DMAc) and the antisolvent is an aqueous acidic solution with a pH of less than 5, preferably a hydrochloric acid solution, more preferable a 0.1 N hydrochloric acid.

In an embodiment, the ratio of the solvent to the antisolvent is between 1:1 and 1:50 or between 1:5 and 1:10.

In an embodiment, the precipitate of step ii) is washed with additional anti-solvent.

In an embodiment, the pharmaceutically acceptable carrier comprises one or more of a filler, a disintegrant, a lubricant, a binder and an anti-nucleating agent.

In an embodiment, the filler is microcrystalline cellulose, a lactose or mixtures thereof.

In an embodiment, the disintegrant is sodium starch glycolate.

In an embodiment, the lubricant is magnesium stearate.

In an embodiment, the binder is hydroxypropylene cellulose.

In an embodiment, the anti-nucleating agent is methyl cellulose A4C or hydroxypropyl methylcellulose E50.

An embodiment of the invention is a process to make the pharmaceutical composition comprising i) dissolving the compound of Formula (I) and a polymer in a solvent;

ii) combing the solution of step i) with an anti-solvent to precipitate a dispersion of the compound of Formula (I) in the polymer;

iii) blending the dispersion of step ii) with a pharmaceutically acceptable carrier;

wherein the pharmaceutical carrier comprises one or more excipients selected from a filler, a lubricant, a binder, an anti-nucleating agent and a disintegrant.

Methods of Treatment

A method of treating atopic dermatitis comprising administering to an animal in need thereof, an effective amount of the pharmaceutical composition comprising the compound of Formula (I) and a HPMCAS polymer.

A method of treating atopic dermatitis comprising administering to an animal in need thereof, an effective amount of the pharmaceutical composition comprising the compound of Formula (I) and a HPMCAS polymer, wherein the effective amount of the compound of Formula (I) is between about 0.1 and about 2.0 mg/kg body weight.

The pharmaceutical composition is administered orally.

In an embodiment, the animal to be treated is a companion animal mammal. In another embodiment, the companion animal is a dog, a cat or a horse. In another embodiment, the companion animal is a dog.

In an embodiment of the invention, the dose of the active ingredient administered to the animal is from about 0.1 mg/kg to about 2.0 mg/kg, about 0.2 to about 0.8 mg/kg, about 0.3 to about 0.7 mg/kg, about 0.5 mg/kg, about 1.0 mg/kg.

In an embodiment, the composition is administered without food.

In an embodiment, the composition is administered in a fed state.

In an embodiment, the composition is administered in a fasted state.

In an embodiment, the pharmaceutical composition is administered once a day for 28 days.

In another embodiment, the pharmaceutical composition is administered twice a day for 14 days, followed by once a day for 14 days.

In other embodiment, the administration of the pharmaceutical composition is administered daily beyond the aforementioned dosing regimens as long as medically necessary including for the life of the animal.

In an embodiment, the pharmaceutical composition is administered once a day as long as medically necessary including for the life of the animal.

In an embodiment, the pharmaceutical composition is administered twice a day for up to 14 days, followed by once a day as long as medically necessary including for the life of the animal.

In an embodiment, the pharmaceutical composition is administered twice a day for one day, two days, three days, four days, five days, six days, seven days, eight days, nine days, ten days, eleven days, twelve days or thirteen days, followed by once a day as long as medically necessary including for the life of the animal.

The pharmaceutical composition of the compound of Formula (I) may be administered in combination with antihistamines, antibiotics, antipruritics, and ceramides. These combinations may be administered simultaneously or sequentially.

EXAMPLES

Example 1—Polymer Matrix Selection

Preliminary trials with the compound of Formula (I) were conducted with a number of polymers (vinylpyrrolidone-vinyl acetate copolymers (VA64), hydroxypropyl methyl cellulose (HPMC), and HPMCAS) with volatile solvents (tetrahydrofuran (THF), methyl ethyl ketone (MEK), methyl tert-butyl ether (MTBE) and heptane). These experiments resulted in solutions, semi-solids, solids containing crystalline material, or amorphous solids not conducive to downstream processing such as milling and compression. A number of solvents and polymers used to make ASDs with the compound of Formula (I) resulted in gummy material which is unable to be blended and compressed. Others solvent/polymer combinations resulted in extremely hard materials which were unable to be milled to uniform particle size by conventional mills The amorphous solid dispersions of the compound of Formula (I) listed below were prepared at 10 mL scale using the IKA Ultra-Turrax Tube Drive at 10 mL scale. The characteristics of the ASDs produced are also reported below.

| Polymer | Solvent | Anti-Solvent | Observation |
|---|---|---|---|
| HPMCAS | DMAc | MTBE | Gummy |
| HPMCAS | THF | MTBE | Amorphous Phase Separation, High Residual Solvent |
| HPMCAS | MEK | Heptane | Unable to Mill |
| HPMCAS | MEK | MTBE | Unable to Mill, High Residual Solvent |
| HPMCAS | THF | Heptane | Amorphous Phase Separation, High Residual Solvent |
| HPMC | DMAc | IPA | Gummy |
| HPMC | DMAc | Ethanol | Gummy |
| VA64 | DMAc | IPA | Gummy |
| VA64 | DMAc | Ethanol | Gummy |

Next aqueous solvent systems were assessed and success was found with HPMCAS in combination with a DMAc: 0.1N Hydrochloric acid solvent:anti-solvent system.

| Polymer | Solvent | Anti-Solvent | Observation |
|---|---|---|---|
| HPMCAS | DMAc | 0.1N HCl | Solid, amorphous |

Samples of amorphous solid dispersions (ASD) with differing ratios of the HPMACAS polymer and the active ingredient, the compound of Formula (I) were prepared and analyzed by powder x-ray diffraction (PXRD) to determine the amount of amorphous compound present in the ASD. ASDs with 3:1 ratio of polymer to compound showed a small amount of crystallinity. However, ASDs with ratios polymer to compound of 5:1 and 10:1 showed no substantial crystallinity. See FIG. 1. The base line trace was of the crystalline form of the compound of Formula (I). The other traces showed the crystallinity of the several ASDs with varying ratios of api to polymer. The trace of the ASD with a 3:1 ratio of polymer to compound showed the most similarity to the crystalline trace and therefore indicates a significant amount of crystalline form of the compound of Formula (I) was present in the 3:1 ASD. The traces of the ASDs with 5:1, 7:1 and 10:1 ratio of polymer to compound showed less similarity to the crystalline trace and therefore indicates no significant amounts of crystalline form of the compound of Formula (I) were present in each of these ASDs.

Example 2—Co-Precipitate Formulation of the Compound of Formula (I) and Hydroxypropyl Methylcellulose Acetate Succinate (HPMCAS)

In this process, the compound of Formula (I) (i.e. the active ingredient (API)) and a polymer (hydroxypropyl methylcellulose acetate succinate, grade L) were dissolved into a solvent (DMAc). The API-Polymer solution was then rapidly precipitated in an anti-solvent (0.1N HCl) under high shear in a rotor-stator homogenizer. The precipitation and the washes conditions were accomplished using a 1:10 solvent:ant-solvent ratio. The precipitation was followed by a 10× slurry wash and then by a 5× displacement wash. An amorphous solid dispersion of the compound and the polymer was formed and compressed into tablets.

The amorphous solid dispersion (ASD) with a ratio of 10:1 of HPMCAS-L polymer to the compound of Formula (I) was formed by dissolving 750 mg of the compound and 7500 mg of HPMCAS-L polymer in 56.25 mL DMAc solvent. This solution was stirred overnight to ensure full dissolution. Next, 500 mL of cold 0.1N HCl was added to a 1 L beaker. An IKA T25 rotor-stator homogenizer was added into the beaker and turned to 20,000 RPM. 50 mL of the compound/polymer solution was then added by syringe through a 14 G needle into the high shear zone of the rotor stator mixer. The compound/polymer mixture rapidly precipitated and was mixed for an additional 2 minutes on ice. The resulting suspension was filtered and added to 500 mL fresh cold 0.1N HCl. The resulting suspension was slurry washed for an additional 2 minutes and then filtered. 250 mL of fresh cold 0.1N HCl was then added to the top of the resulting cake and washed by displacement. The final cake was then dried under vacuum and nitrogen sweep overnight. The resulting dry ASD had an assay of 82.5%. To manufacture tablets, 4850 mg of the ASD was added to 3050 mg microcrystalline cellulose, 1500 mg lactose monohydrate, and 500 mg sodium starch glycolate and blended with a Turbula mixer for 15 minutes at 49 RPM. 100 mg magnesium stearate was then added and mixed for an additional 5 minutes. Tablets were then manufactured with a carver press pressing 5⁄16" round standard concave tablets at 1500 lbs.

The amorphous solid dispersion (ASD) with a ratio of 5:1 of HPMCAS-L polymer to the compound of Formula (I) was formed by dissolving 1500 mg of the compound and 7500 mg of HPMCAS-L polymer in 56.25 mL DMAc solvent. The solution was stirred overnight to ensure full dissolution. Next, 500 mL of cold 0.1N HCl was added to a 1 L beaker. An IKA T25 rotor-stator homogenizer was added into the beaker and turned to 20,000 RPM. 50 mL of the compound/polymer solution was then added by syringe through a 14 G needle into the high shear zone of the rotor stator mixer. The compound/polymer mixture rapidly precipitated and was mixed for an additional 2 minutes on ice. The resulting suspension was filtered and added to 500 mL fresh cold 0.1N HCl. The resulting suspension was slurry washed for an additional 2 minutes and then filtered. 250 mL of fresh cold 0.1N HCl was then added to the top of the resulting cake and washed by displacement. The final cake was then dried under vacuum and nitrogen sweep overnight. The resulting ASD had an assay of 93.3%. 2150 mg of the intermediate was added to 4750 mg microcrystalline cellulose, 2500 mg lactose monohydrate, and 500 mg sodium starch glycolate and blended with a Turbula mixer for 15 minutes at 49 RPM. 100 mg magnesium stearate was then added and mixed for an additional 5 minutes. Tablets were then manufactured with a carver press pressing 5⁄16" round standard concave tablets at 1500 lbs.

Tablets containing crystalline compound of Formula (I) were manufactured by blending 150 mg of the compound, 3375 mg of microcrystalline cellulose, 3525 mg lactose monohydrate, and 375 mg sodium starch glycolate with a Turbula mixer for 15 minutes at 49 RPM. Tablets were then manufactured with a carver press pressing 5⁄16" round standard concave tablets at 1500 lbs.

Example 3—Bioavailability of the Compound of Formula (I)

A pharmacokinetic (PK) study of the above ASD and crystalline formulations was conducted in fed and fasted dogs. For fasted groups, animals were fasted overnight with food given 4 hours after dosing. A blood sample was collected at this time prior to the animals being fed. Fed Animals were provided daily rations after an overnight fast approximately 30 minutes prior to administration of the pharmaceutical compositions.

Figure 2:
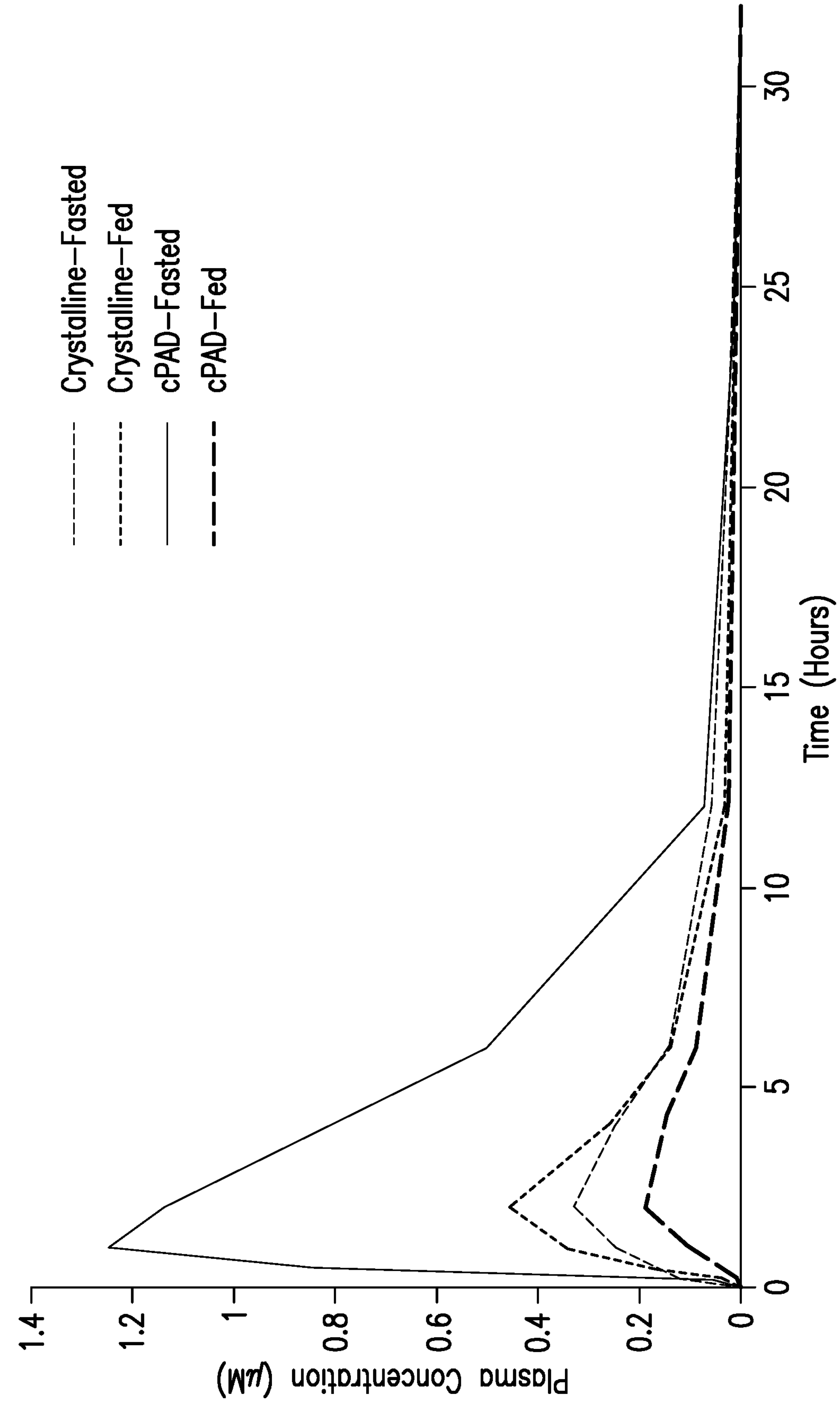
FIG. 2—Pharmacokinetic (PK) study demonstrating the bioavailability of amorphous solid dispersions of the compound of Formula (I) in Hydroxypropyl methylcellulose acetate succinate (HPMCAS).

Results suggest that in the fasted state, significant improvement in bioavailability is achieved for the formulation containing the compound of Formula (I) in an amorphous solid dispersion (ASD) formulation with HPMCAS-L. However, in the fed state, there is no significant change in bioavailability as compared to formulation prepared with crystalline compound of Formula (I). See FIG. 2.

Example 4—Anti-Nucleation Agents

Figure 3:
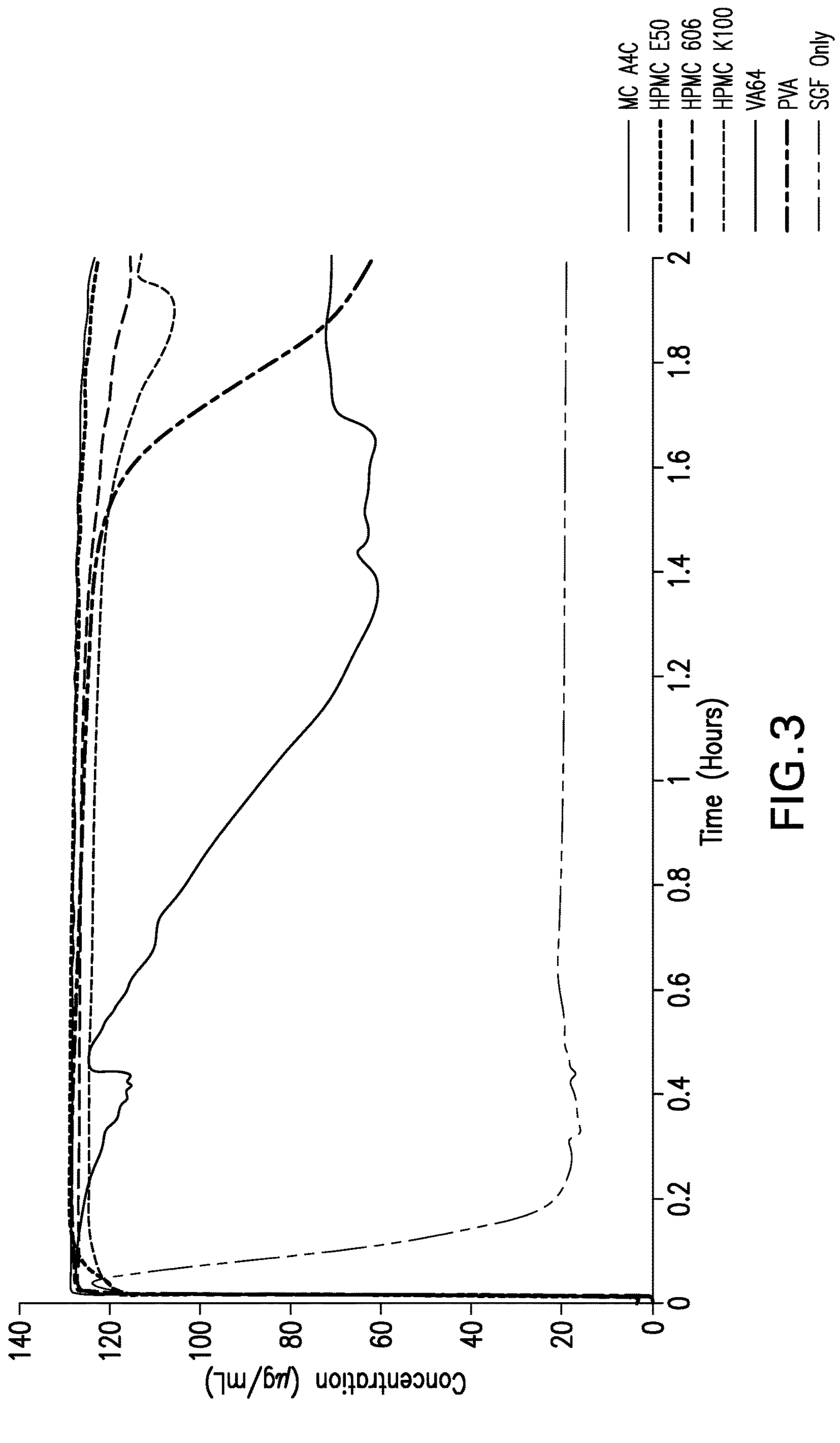
FIG. 3—Several anti-nucleating polymers were assessed for ability to maintain the compound of Formula (I) in an in vitro screen.

In an attempt to improve the bioavailability of the compound of Formula (I) in animals administered in the fed state, anti-nucleating agents were added to the pharmaceutical composition to decrease the potential for crystallization of the compound. Several anti-nucleation polymers were assessed for ability to maintain the compound of Formula (I) in an in vitro screen. 0.5% solution of each anti-nucleating polymer was prepared in simulated gastric fluid, pH 1.8. 75 uL of 10 mg/mL API in DMSO was added into 5 mL of the 0.5% polymer solution and monitored by PION UV probe for 2 hours at 272 nm. See FIG. 3. The concentration of the compound of Formula (I) was maintained during the entire 2 hour test when the anti-nucleating polymers methylcellulose A4C (MC A4C) and hydroxypropyl methylcellulose E50 (HPMC E50) were used. When the other polymers were used, the concentration of the compound of Formula (I) was initially maintained but finally was reduced before the 2 hour test was completed. This is in contrast to the control sample with only simulate gastric fluid (SGF) where the concentration of the compound of Formula (I) dropped almost immediately The results suggest that MC A4C and HPMC E50 are suitable anti-nucleation polymers to improve bioavailability in the fed state as these polymers are capable of maintaining supersaturated levels of the compound of Formula (I) for extended periods in comparison to the other polymers tested.

Example 5—Efficacy Study

The compound is being evaluated in a masked and randomized proof-of-concept study in dogs with a diagnosis of atopic dermatitis. The objective of this study is to evaluate the efficacy and tolerability of the compound against atopic dermatitis in client-owned dogs. The compound will be evaluated at two doses and will be compared to a placebo control. Dogs will be dosed orally twice daily for up to 14 days followed by once daily for up to 28 days, or once daily for 28 days, and will be evaluated for pruritus and skin lesions using the Pruritus Visual Analog Scale (PVAS) and Canine Atopic Dermatitis Extent and Severity Index (CADESI-4) scoring tools, respectively.

The Canine Atopic Dermatitis Extent and Severity Index (CADESI-4) is a severity scale used to grade skin lesions in clinical trials for treatment of dogs with atopic dermatitis (AD). Three lesion types (erythema, lichenification and alopecia/excoriation) are scored from 0 to 3 at each of 20 body sites, for a maximal score of 180, with proposed benchmarks for mild, moderate and severe AD skin lesions of 10, 35 and 60, respectively. CADESI-4: Thierry, O., Manolis, S., Nuttall, T., Bensignor, E., Griffin, C., Hill, P., for the International Committee on Allergic Diseases of Animals (ICADA). Validation of the Canine Atopic Dermatitis Extent and Severity Index (CADESI)-4, a simplified severity scale for assessing skin lesions of atopic dermatitis in dogs. Vet, Dermatol. 25:77-e25, 2014

The Pruritus Visual Analog Scale (PVAS) is a visual analog scale that contains features of both the severity of itching and behaviors associated with itching. It is commonly used to determine the severity of pruritus in clinical trials for treatment of dogs with AD. PVAS: Hill, P. B., Lau, P., and Rybnicek, J. Development of an owner-assessed scale to measure the severity of pruritus in dogs. Vet. Dermatol. 18:301-308, 2007.

The invention claimed is:

1. A solid pharmaceutical composition comprising
   a) a pharmaceutically effective amount of a compound of Formula (I)

Formula (I)

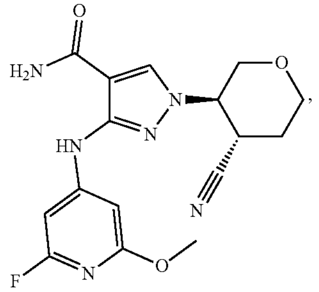

dispersed in a hydroxypropyl methylcellulose acetate succinate (HPMCAS) polymer matrix; and
   b) a pharmaceutically acceptable carrier;

wherein the compound of Formula (I) is present in substantially an amorphous form; and wherein the pharmaceutical composition is a tablet and wherein at least 80% of the compound of Formula (I) is in amorphous form and the ratio of the polymer to the compound of Formula (I) in the dispersion is between about 10:1 and about 5:1.

2. The pharmaceutical composition of claim 1, wherein the hydroxypropyl methylcellulose acetate succinate polymer is L grade (HPMCAS-L).

3. The pharmaceutical composition of claim 1, wherein the amount of the compound of Formula (I) in the pharmaceutical composition is between about 0.5 and about 10% or is between about 1.0 and about 5.0% or is about 2% (w/w).

4. The pharmaceutical composition of claim 1, wherein the amount of HPMCAS polymer in the pharmaceutical composition is between about 10 and about 30% or is between about 15 and about 25% or is about 20% (w/w).

5. The pharmaceutical composition of claim 1, wherein the pharmaceutically acceptable carrier comprises one or more excipients selected from a filler, a lubricant, a binder, an anti-nucleating agent and a disintegrant.

6. The pharmaceutical composition of claim 5, wherein the filler is a microcrystalline cellulose, a lactose or mixtures thereof.

7. The pharmaceutical composition of claim 5, wherein the lubricant is magnesium stearate.

8. The pharmaceutical composition of claim 5, wherein the disintegrant is sodium starch glycolate.

9. The pharmaceutical composition of claim 5, wherein the binder is hydroxypropyl cellulose.

10. The pharmaceutical composition of claim 5, wherein the anti-nucleating agent is methyl cellulose A4C or hydroxypropyl methylcellulose E50.

11. A solid pharmaceutical composition comprising a compound of Formula (I)

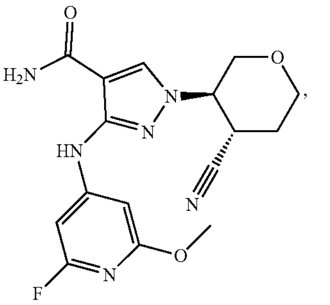 [SMILES: COc1cc(Nc2nn([C@H]3COCC[C@@H]3C#N)cc2C(N)=O)cc(F)n1]

dispersed in a hydroxypropyl methylcellulose acetate succinate (HPMCAS) polymer matrix wherein in the solid pharmaceutical composition comprises
   a) about 0.5 to about 10% w/w of the compound of Formula (1);
   b) about 10 to about 30% w/w of HPMCAS;
   c) about 0.25 to about 1.5% w/w of magnesium stearate;
   d) about 0 to about 75% w/w of microcrystalline cellulose;
   e) about 0 to about 75% w/w of lactose monohydrate; and
   f) optionally about 0 to 5% w/w of hydroxypropyl cellulose;

wherein the combined w/w percentages of microcrystalline cellulose and lactose monohydrate must be at least 40%.

* * * * *